(12) United States Patent
Levine et al.

(10) Patent No.: US 7,285,295 B2
(45) Date of Patent: Oct. 23, 2007

(54) TRANSMUCOSAL ORAL DELIVERY DEVICE

(75) Inventors: William Levine, Jerusalem (IL); Aron Saffer, Jerusalem (IL)

(73) Assignee: Izun Pharmaceuticals Corp., New York, NY (US)

( * ) Notice: Subject to any disclaimer, the term of this patent is extended or adjusted under 35 U.S.C. 154(b) by 0 days.

(21) Appl. No.: 11/284,078

(22) Filed: Nov. 21, 2005

(65) Prior Publication Data

US 2006/0110482 A1    May 25, 2006

Related U.S. Application Data

(60) Provisional application No. 60/630,363, filed on Nov. 22, 2004.

(51) Int. Cl.
*A61K 36/00*    (2006.01)

(52) U.S. Cl. ..................................... 424/725

(58) Field of Classification Search ............ None
See application file for complete search history.

(56) References Cited

U.S. PATENT DOCUMENTS 6,576,267 B2 * 6/2003 Gelber et al. ............... 424/725
2003/0003140 A1 * 1/2003 Domb et al. ................ 424/449

* cited by examiner

*Primary Examiner*—Christopher R. Tate
*Assistant Examiner*—Melenie McCormick
(74) *Attorney, Agent, or Firm*—Law Offices of Arthur E. Jackson

(57) ABSTRACT

Provided, among other things, is a method of treating an indication of mucosal or adjacent tissue comprising periodically applying to mucosa at or adjacent to disease affected tissue a delivery device comprising a backing layer and an adhesive reservoir comprising an effective amount of appropriate composition of plant extract(s) comprising extract of *Sambucus nigra*, wherein the adhesive reservoir comprises 30 to 70 polymer by weight, of which a major portion comprises polyacrylic polymer, wherein the delivery device is flexible and tissue conforming.

19 Claims, No Drawings

TRANSMUCOSAL ORAL DELIVERY DEVICE

This application claims the priority of U.S. Provisional Application 60/630,363, filed 22 Nov. 2004.

The present invention relates to devices and methods for delivering *Sambucus nigra*-containing plant extracts, with or without additional extracts, to mucosal tissue.

Historically, the plant world has been the most important source of medicinal agents for the treatment of human and animal disease, and for use as preventative agents in maintaining good health. For at least the last 150 years, Western medicine has been dominated by synthetic and/or highly purified chemical agents. It is now being increasingly recognized that plant extracts can be highly effective agents for the amelioration or treatment of disease. Appropriately selected extracts can have low toxicity and greatly reduced incidence of adverse effects as compared with many synthetic or highly purified drugs. In addition, as plants possess large numbers of pharmaceutically active agents, extracts can exert their activities on a variety of physiologic processes, increasing the range of desired therapeutic effect.

Described in WO 02/094300 are a number of useful combinations of herbal extracts for treating or ameliorating diseases of mucosa.

It has now been discovered that a particular mucosal-adhering delivery device, which has an adhesive reservoir of herbal extract, is remarkably effective in treating gingivitis. In one aspect, the device is believed to be as effective because the delivery form is particularly effective in conforming to and adhering to uneven oral mucosal surfaces. The combination of relevant extracts provides an increase in adhesive strength.

In another aspect, the delivery device allows, after the initial adherence of the device to the mucosa, the backing layer to be removed, while leaving the softer adhesive reservoir of herbal agent adhered to the mucosa. Thus, the delivery device can increase patient comfort, or allows the patient as needed to limit the obstruction of his or her mouth without markedly reducing efficacy.

In another aspect, dye in the backing layer and/or adhesive reservoir of the delivery device is selected and incorporated in an appropriate amount such that the color of the delivery device changes when (i) an appropriate application time has been accomplished or (ii) an appropriate time for removing that backing layer has been reached (at which time the residual adhesive layer may still be delivering herbal agent).

SUMMARY OF THE INVENTION

The invention provides, in one embodiment, a method of treating an indication of mucosal or adjacent tissue comprising periodically applying to mucosa at or adjacent to disease affected tissue a delivery device comprising a backing layer and an adhesive reservoir comprising an effective amount of appropriate composition of plant extract(s) comprising extract of *Sambucus nigra*, wherein the adhesive reservoir comprises 30 to 70 polymer by weight, of which a major portion comprises polyacrylic polymer, wherein the delivery device is flexible and tissue conforming (as described further below).

Also provided in another embodiment is a transmucosal delivery device comprising a backing layer and an adhesive reservoir comprising an effective amount of appropriate composition of plant extract(s) comprising extract of *Sambucus nigra*, wherein the adhesive reservoir comprises 30 to 70 polymer by weight, of which a major portion comprises polyacrylic polymer, wherein the delivery device is flexible and tissue conforming.

Still another embodiment provides a kit for the treatment of an oral disease comprising: transmucosal delivery device comprising a backing layer and an adhesive reservoir comprising an effective amount of appropriate composition of plant extract(s) comprising extract of *Sambucus nigra*; labeling or other instructions describing that (i), when needed, the backing layer may be removed after an initial amount of time less than a recommended treatment time, or (ii) when the delivery device has changed color to a degree indicated the delivery device or the backing layer thereof may be removed.

DETAILED DESCRIPTION OF THE INVENTION

Plant Extracts

Appropriate plant extract compositions for use in the device include extract of *Sambucus nigra* (SN), and may include additional plant extracts of *Allium sativum* (AS), *Calendula officinalis* (CO), *Camellia sinensis* (CS), *Centella asiatica* (CA, also known as Gotu Kola), *Commiphora molmol* (CM), *Echinacea purpurea* (EP), *Gaultheria procumbens* (GP), *Hypericum perforatum* (HP), *Krameria triandra* (KT), *Ligusticum porterii-osha* (LP), *Matricaria recutita, Melissa officinalis, Salix alba, Thymus vulgaris, Uncaria tomentosa, Usnea barbata* or *Vaccinium myrtillus*. The extract compositions can include, for example, *Sambucus nigra* extract in an amount from one of the lower percentages (by weight) recited in the next sentence to 90, 95, 96, 97, 98, 99 or 100%. These lower percentages are 50, 55, 60, 65, 70, 75, 80, 85, 90 or 95%. If a second or third extract is present, it may be present, for example in amount from one of the lower percentages to one of the higher percentages recited in the following sentences. Lower percentages for the second or third extracts can be, for example, 0.5, 1, 2, 5, 10 or 20%. Higher percentages can be, for example, 1, 2, 5, 10, 20, 30, 40 or 50%. These ranges, and any other ranges described in this application, can included or exclude one or both endpoints.

The term "extract" is used herein to include all of the many types of preparations containing an effective amount of active ingredients. Thus, the extracts can be produced by cold extraction techniques using a variety of different extraction solvents including, but not limited to, water, fatty solvents (such as olive oil), and alcoholic solvents (e.g. 70% ethanol). Cold extraction techniques are typically applied to softer parts of the plant such as leaves and flowers, or in cases wherein the desired active components of the plant are heat labile. Alternatively, hot extraction techniques can be used, where such solvents are heated to a temperature above room temperature, with the precise value of said temperature being dependent on factors such as the properties of the chosen solvent and extraction efficacy. Hot extraction techniques are more commonly applied to the harder, tougher parts of the plant, such as bark, woody branches and larger roots. In some cases, sequential extractions need to be performed in more than one solvent, and at different temperatures. Standard procedures for producing plant extracts (including hot extraction, cold extraction and other techniques) are described in many publications including "Medicinal plants: a field guide to the medicinal plants of the Land of Israel (in Hebrew), author: N. Krispil, Har Gilo, Israel, 1986" and "Making plant medicine, author: R. Cech, pub. by Horizon Herbs, 2000".

Exemplary extract compositions by weight percentage include:

| Plant Extract | Composition: | | | | | | | | | | | |
|---|---|---|---|---|---|---|---|---|---|---|---|---|
| | C1 | C2 | C3 | C4 | C5 | C6 | C7 | C8 | C9 | C10 | C11 | C12 |
| SN | 70 | 80 | 90 | 70 | 80 | 90 | | | | | | |
| AS | 30 | 20 | 10 | | | | | | | | | |
| CO | | | | 30 | 20 | 10 | | | | | | |
| CA | | | | | | | 30 | 20 | 10 | | | |
| CM | | | | | | | | | | 30 | 20 | 10 |
| | C13 | C14 | C15 | C16 | C17 | C18 | C19 | C20 | C21 | C22 | C23 | C24 |
| SN | 70 | 70 | 70 | 70 | 70 | 70 | 70 | 70 | 70 | 70 | 70 | 70 |
| AS | 20 | 20 | 20 | 20 | 20 | | | | | | | |
| CO | 10 | | | | | 20 | 20 | 20 | 20 | | | |
| CA | | 10 | | | | 10 | | | | 20 | 20 | 20 |
| CM | | | 10 | | | | 10 | | | 10 | | |
| EP | | | | 10 | | | | 10 | | | 10 | |
| GP | | | | | 10 | | | | 10 | | | 10 |
| | C25 | C26 | C27 | C28 | C29 | C30 | C31 | C32 | C33 | C34 | C35 | C36 |
| SN | 80 | 80 | 80 | 80 | 80 | 80 | 80 | 80 | 80 | 80 | 80 | 80 |
| AS | 10 | 10 | 10 | 10 | 10 | | | | | | | |
| CO | 10 | | | | | 10 | 10 | 10 | 10 | | | |
| CA | | 10 | | | | 10 | | | | 10 | 10 | 10 |
| CM | | | 10 | | | | 10 | | | 10 | | |
| EP | | | | 10 | | | | 10 | | | 10 | |
| GP | | | | | 10 | | | | 10 | | | 10 |
| | C37 | C38 | C39 | C40 | C41 | C42 | | C44 | C45 | C46 | C47 | C48 |
| SN | 90 | 90 | 90 | 90 | 90 | 90 | | 90 | 90 | 90 | 90 | 90 |
| AS | 10 | 9 | 8 | 7 | 6 | 5 | | 9 | 8 | 7 | 6 | 5 |
| CO | | 1 | 2 | 3 | 4 | 5 | | | | | | |
| CA | | | | | | | | 1 | 2 | 3 | 4 | 5 |
| | C49 | C50 | C51 | C52 | C53 | C54 | | C56 | C57 | C58 | C59 | C60 |
| SN | 90 | 90 | 90 | 90 | 90 | 90 | | 90 | 90 | 90 | 90 | 90 |
| AS | 10 | 9 | 8 | 7 | 6 | 5 | | 9 | 8 | 7 | 6 | 5 |
| CM | | 1 | 2 | 3 | 4 | 5 | | | | | | |
| EP | | | | | | | | 1 | 2 | 3 | 4 | 5 |
| | C61 | C62 | C63 | C64 | C65 | C66 | | | | | | |
| SN | 90 | 90 | 90 | 90 | 90 | 90 | | | | | | |
| AS | 10 | 9 | 8 | 7 | 6 | 5 | | | | | | |
| GP | | 1 | 2 | 3 | 4 | 5 | | | | | | |
| | C67 | C68 | C69 | C70 | C71 | C72 | | C74 | C75 | C76 | C77 | C78 |
| SN | 90 | 90 | 90 | 90 | 90 | 90 | | 90 | 90 | 90 | 90 | 90 |
| CO | 10 | 9 | 8 | 7 | 6 | 5 | | 9 | 8 | 7 | 6 | 5 |
| CA | | 1 | 2 | 3 | 4 | 5 | | | | | | |
| CM | | | | | | | | 1 | 2 | 3 | 4 | 5 |
| | C79 | C80 | C81 | C82 | C83 | C84 | | C86 | C87 | C88 | C89 | C90 |
| SN | 90 | 90 | 90 | 90 | 90 | 90 | | 90 | 90 | 90 | 90 | 90 |
| CM | 10 | 9 | 8 | 7 | 6 | 5 | | 9 | 8 | 7 | 6 | 5 |
| EP | | 1 | 2 | 3 | 4 | 5 | | | | | | |
| GP | | | | | | | | 1 | 2 | 3 | 4 | 5 |
| | C91 | C92 | C93 | C94 | C95 | C96 | | C98 | C99 | C100 | C101 | C102 |
| SN | 90 | 90 | 90 | 90 | 90 | 90 | | 90 | 90 | 90 | 90 | 90 |
| CA | 10 | 9 | 8 | 7 | 6 | 5 | | 9 | 8 | 7 | 6 | 5 |
| CM | | 1 | 2 | 3 | 4 | 5 | | | | | | |
| EP | | | | | | | | 1 | 2 | 3 | 4 | 5 |

-continued

| Plant Extract | Composition: | | | | | | | | | | |
|---|---|---|---|---|---|---|---|---|---|---|---|
| | C103 | C104 | C105 | C106 | C107 | C108 | C110 | C111 | C112 | C113 | C114 |
| SN | 90 | 90 | 90 | 90 | 90 | 90 | 90 | 90 | 90 | 90 | 90 |
| EP | 10 | 9 | 8 | 7 | 6 | 5 | 9 | 8 | 7 | 6 | 5 |
| GP | | 1 | 2 | 3 | 4 | 5 | | | | | |
| HP | | | | | | | 1 | 2 | 3 | 4 | 5 |
| | C115 | C116 | C117 | C118 | C119 | C120 | C122 | C123 | C124 | C125 | C126 |
| SN | 90 | 90 | 90 | 90 | 90 | 90 | 90 | 90 | 90 | 90 | 90 |
| EP | 10 | 9 | 8 | 7 | 6 | 5 | 9 | 8 | 7 | 6 | 5 |
| KT | | 1 | 2 | 3 | 4 | 5 | | | | | |
| LP | | | | | | | 1 | 2 | 3 | 4 | 5 |

The above amounts provide exemplary useful amounts ±0.5% for amounts from 1–2%, ±0.5 or 1% for amounts from 3–5%, ±0.5, 1 or 2% for amounts from 6–10%, ±1, 2, 3, 4 or 5% for amounts from 70–90% (with the foregoing percentage ranges being of the total extract amount by weight).

In some embodiments, the solids from the extract(s) typically contribute amounts to the adhesive reservoir layer from one of the following lower endpoints or from one of the following upper endpoints. The lower endpoints are 10, 15, 20, 25 and 30 weight percent. The upper endpoints are 15, 20, 25, 30, 35, 40 and 45 weight percent. The percent of such solids in the adhesive reservoir layer can be, for example, approximately 30.0, 30.1, 30.2 and so in increments of 0.1 up to 40.0.

Polymer for Adhesive Reservoir Layer

In some embodiments, the polymers contribute amounts to the adhesive reservoir layer from one of the following lower endpoints or from one of the following upper endpoints. The lower endpoints are 30, 35, 40, 45 and 50 weight percent. The upper endpoints are 35, 40, 45, 50, 55, 60, 65 and 70 weight percent. For example, the polymers can comprise 35 to 65 wt. %, or 40 to 60 wt. %. For this purpose polymers comprise synthetic polymers, natural polymer products, or derivatives of natural polymer products, but not polymers that may happen to be found in the plant extracts.

The major portion of the polymers comprises polyacrylic acid polymers such as the cross-linked carbomers sold as Carbopol™ (Noveon, Cleveland, Ohio) or Eudragit™ (Röhm GmbH & Co. KG, Darmstadt, German). For example, Carbopol 971 can be used. The carbomer weight percentage of the polymers can be, for example, from one of the following lower endpoints or from one of the following upper endpoints. The lower endpoints are 51, 55, 60, 65 and 75 weight percent. The upper endpoints are 60, 65, 70, 80, 85, 90, 95, 98, 99 and 100 weight percent. For example, the carbomer polymers can comprise 65 to 85 wt. %, or 70 to 80 wt. %.

For example, the polymer portion of the adhesive reservoir layer can be approximately 45.0% (by wt.), 45.1%, 45.2% and so in increments of 0.1% up to 55.0%. The weight percent carbomer in the polymers can be, for example, 70, 70.1, 70.2 and so on in increments of 0.1 to 80.0.

The other polymers can be polymers that affect the rate of hydration or mucosal adhesion properties of the adhesive reservoir layer. Such polymers can be, for example, carboboxymethylcellulose, cellulose acetate, ethylcellulose, hydroxyethylcellulose, hydroxypropylmethylcellulose (HPMC, such as Pharmacoat 606™, Shin-Etsu Chemical Company Ltd., Japan), nitrocellulose, polyoxyethylene/polyoxypropylene polymers, copolymers or block copolymers, polyvinylpyrrolidone polymers or derivatives, and the like.

In one embodiment, the weight percentage (with respect to the polymers) of a second, water-soluble polymer can be, for example, from one of the following lower endpoints or from one of the following upper endpoints. The lower endpoints are 5, 6, 7, 8, 9 and 10 weight percent. The upper endpoints are 10, 12, 14, 16, 18 and 20 weight percent.

Other Compoents for Adhesive Reservoir Layer

Among other optional components of the adhesive reservoir are pigments, such as for example titanium dioxide or zinc oxide. Flavoring agents may be included, such as strawberry flavor. Further optional components include moisturizing agents, antioxidants, antimicrobials, and the like. Moisturizing agents include, for example, glycerin, sorbitol, propylene glycol, and the like. The moisturizer weight percentage of the adhesive reservoir can be, for example, from one of the following lower endpoints or from one of the following upper endpoints. The lower endpoints are 1, 2 and 4 weight percent. The upper endpoints are 2, 4 and 10 weight percent. The percent of such moisturizer in the adhesive reservoir layer can be, for example, 4.0, 4.1, 4.2 and so in increments of 0.1 up to 12.0.

In one embodiment, the adhesive reservoir layer is essentially lacking in any added amphipathic intradermal penetration enhancer, such as oleic acid or triglyceride, excepting any such amphipathic molecule found in the plant extracts.

Backing Layer

A range of backing layers can be used to separate the adhesive reservoir from non-targeted regions of the patient's body. The backing layer can be, for example, a flexible polymer film such as, without limitation, a polyester film. One such film is a 15 micron thick polyester film (e.g., from Mitsubishi, Japan). Suitable materials for the backing layer include, without limitation, polyethylene, polyurethane, polyester, ethylene vinyl acetate, acrylonitrile, cellophane, cellulose acetate, cellulosics, ethylcellulose, ethylene vinyl acetate (EVA) copolymers, plasticized vinylacetate-vinyl-chloride copolymers, polyethylene terephthalate polymers, nylons, rayon, polypropylene, polyvinyl alcohol, polyvinyl chloride, metalized polyester films, polyvinylidene chloride, polycarbonate, polystyrene, and aluminum foil. The backing layer can, for example, contain polymers and excipients selected to limit outward diffusion of herbal agent.

The adhesive can be layered on the backing film for example by coating the backing film with an adhesive mixture and removing any carrier solvent for the adhesive mixture. Or, for example, the adhesive can be formed on a release layer, and the backing layer formed or layered on the adhesive.

In one embodiment, the backing layer is made from a suspension/solution of hydrophobic polymer, gum and oil in a solvent. The suspension/solution can be coated onto the adhesive, and dried to remove the solvent. Suitable polymers may include cellulose derivatives such ethylcellulose or cellulose acetate, polyethylene, methacrylate polymers and high molecular weight polyvinylalcohols, and the like.

The backing layer can include coloring agent(s). The coloring agents can be selected to provide a color change when it is appropriate during use to remove the delivery device or the backing layer thereof. The selection can be based on the solubility properties of the agent, as may be modified by other components of the backing layer, and on amounts of coloring agent. Suitable coloring agents include, without limitation, Colour E172 red, titanium dioxide, and mixtures thereof.

Labeling carried with the packaging for the delivery device can contain color charts or other indicia indicating when it is appropriate to remove the delivery device or the backing layer of the delivery device.

Illustrative Indications; Treatment Parameters

Indications treated with the methods and devices of the invention include any indication of mucosal tissue, or tissue sufficiently adjacent to mucosal tissue, treatable with the plant extracts described. For example, oral indications and microbial indications (such as microbial lesions) can be treated with the methods and devices.

Oral indications appropriate for treatment with the invention include, without limitation, periodontal disease, gingivitis, aphthous ulceration (canker sores), mechanical trauma, thermal trauma, the oral lesions or eruptions of lichen planus, bullous pemphigoid, pemphigus vulgaris, dermatitis herpetiformis or angular chelitis, recurrent herpes, or other microbial (including viral) eruptions of the oral mucosa.

The device is periodically applied to affected mucosal tissue or to mucosal tissue adjacent to the affected tissue. For example, the device can be applied once, twice or three times daily. The device is left in place for example for 12, 30, 60, 120, 240 minutes or more on each application.

Other Parameters

The adhesiveness of the delivery devices can be tested with the in vitro procedure described in Chary et al., "In Vitro and In Vivo Adhesion Testing of Mucoadhesive Drug Delivery Systems, *Drug Development and Industrial Pharmacy* 25: 685–90, 1999.

The following examples further illustrate the present invention, but of course, should not be construed as in any way limiting its scope.

EXAMPLE

To make the adhesive layer, EtOH (4.2 g) are stirred with Pharmacoat 606 (HPMC, 1.19 g) and stirred for 30 min. to form a suspension. Using a mechanical mixer (an air driven Venturi-stirrer), Carbopol 971 (3.95 g) is mixed with the suspension for 60 min to obtain a homogenous white gel. Separately, titanium oxide (0.12 g) is mixed with anhydrous glycerin (0.79 g), then added to the white gel. Flavoring agent (0.4 g) and herbal extract(s) (3.56 g extract solid in 96% EtOH) are also added. The mixture is stirred slowly overnight with degassing.

The mixture is coated onto a 988 $cm^2$ piece of release liner using a Erichsen coater set to provide a 2 mm wet coating layer. Drying is conducted first at room temperature (20 min), then at 50° C. (10 min), and finally at 60° C. (15 min).

To make the backing layer, ethylcellulose (3.95 g) is scattered into EtOH (33.6 g) and stirred until the polymer is dissolved. Colour E172 red (0.08 g in 2 mL water) is then added. Separately, titanium oxide (0.1 g) is mixed with caster oil (1.98 g), then added to the polymer solution. Next, polysorbate (0.1 g) is added and stirred to dissolution. Then, Acaciae gum (1.49 g) is added and stirred to dissolution. The solution/suspension can be degassed.

The mixture is coated onto the dried adhesive layer using the Erichsen coater set to provide a 1 mm wet coating layer. Drying is conducted first at room temperature (10 min), and then at 60° C. (15 min). The dried backing layer is a light red. In use, the color fades to pinkish-white after an hour, at which point, at least for some extract combinations, it is believed that the delivery device has been in place for a treatment appropriate amount of time.

A punching machine is used to obtain 1.25 $cm^2$ transdermal devices. The transdermal devices are separated from the release liner and packaged in a heat sealable composite foil.

Additional Definitions

The following terms shall have, for the purposes of this application, the respective meanings set forth below.

Effective Amount

To treat the indications of the invention, an effective amount of a pharmaceutical compound will be recognized by clinicians but includes an amount effective to treat, reduce, alleviate, ameliorate, eliminate or prevent one or more symptoms of the disease sought to be treated or the condition sought to be avoided or treated, or to otherwise produce a clinically recognizable favorable change in the pathology of the disease or condition. Thus, an effective amount can be, for example, an amount that reduces the severity or duration of oral lesions, ulcerations, bleeding, irritation, swelling, erythema, or the like.

Flexible and Tissue Conforming

A delivery device is flexible and tissue conforming if it is flexible prior to application to mucosal tissue and if an otherwise equivalent device of 1 cm diameter can be conformed to a patient's gums, irrespective of whether or not any wetting of the device by the mucosal tissue aids in conforming the device to the gums.

Microbial Infections

Microbial infections include, without limitation, bacterial, mycobacterial, fungal and viral infections.

Treatment

Treatment" means the management and care of a patient for the purpose of combating a disease, disorder or condition. The term is intended to include the delaying of the progression of the disease, disorder or condition, the alleviation, amelioration or relief of symptoms and complications, and/or the cure or elimination of the disease, disorder or condition. The animal to be treated can be a mammal, in particular a human being.

Publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. A method of treating a disease-affected mucosal tissue or a tissue adjacent thereto comprising periodically applying to the disease-affected or adjacent tissue a delivery device comprising a backing layer and an adhesive reservoir containing an effective amount of a plant extract composition comprising an extract of *Sambucus nigra*, wherein the adhesive reservoir further comprises a polymer that is 30 to 70 percent of the adhesive reservoir by weight, of which a major portion of the polymer comprises a polyacrylic polymer, wherein the delivery device is flexible and tissue conforming and wherein the backing layer is made by coating a suspension/solution comprising a hydrophobic polymer, a gum, and an oil in a solvent onto the adhesive reservoir and removing the solvent.

2. The method of claim 1, wherein the indication is of the oral cavity.

3. The method of claim 2, wherein the indication is periodontal disease.

4. The method of claim 1, wherein the indication is gingivitis.

5. A transmucosal delivery device comprising a backing layer and an adhesive reservoir containing an effective amount of a plant extract composition comprising an extract of *Sambucus nigra*, wherein the adhesive reservoir further comprises a polymer that is 30 to 70 percent of the adhesive reservoir by weight, of which a major portion of the polymer comprises a polyacrylic polymer, wherein the delivery device is flexible and tissue conforming and wherein the backing layer is made by coating a suspension/solution comprising a hydrophobic polymer, a gum, and an oil in a solvent onto the adhesive reservoir and removing the solvent.

6. The transmucosal delivery device of claim 5, wherein the concentration of the extract of *Sambucus nigra* ranges 51 to 100% by weight of the plant extract composition within the adhesive reservoir.

7. The transmucosal delivery device of claim 6, wherein the plant extract composition further comprises a second plant extract and wherein the concentration of the second plant extract ranges from 1 to 50% by weight of the plant extract composition within the adhesive reservoir.

8. The transmucosal delivery device of claim 7, wherein the plant extract composition further comprises a third plant extract and wherein the concentration of the third plant extract ranges from 0.5 to 5% by weight of the plant extract composition within the adhesive reservoir.

9. The transmucosal delivery device of claim 5, wherein the polymers comprise carbomer polymers, and wherein the concentration of the carbomer polymers ranges from 65 to 85% by weight of the polymers within the adhesive reservoir.

10. The transmucosal delivery device of claim 5, wherein the polymers comprise carbomer polymers, and wherein the concentration of the carbomer polymers ranges from 70 to 80% by weight of the polymers within the adhesive reservoir.

11. The transmucosal delivery device of claim 5, wherein the concentration of the polymers ranges from 40 to 60 percent within the adhesive reservoir by weight.

12. The transmucosal delivery device of claim 11, wherein the polymers comprise carbomer polymers, and wherein the concentration of the carbomer polymers ranges from 65 to 85% by weight of the polymers within the adhesive reservoir.

13. The transmucosal delivery device of claim 11, wherein the polymers comprise carbomer polymers, and wherein the concentration of the carbomer polymers ranges from 70 to 80% by weight of the polymers within the adhesive reservoir.

14. The transmucosal delivery device of claim 5, wherein the concentration of the polymers ranges from 45 to 55 percent within the adhesive reservoir by weight.

15. The transmucosal delivery device of claim 14, wherein the polymers comprise carbomer polymers, and wherein the concentration of the carbomer polymers ranges from 65 to 85% by weight of the polymers within the adhesive reservoir.

16. The transmucosal delivery device of claim 14, wherein the polymers comprise carbomer polymers, and wherein the concentration of the carbomer polymers ranges from 70 to 80% by weight of the polymers within the adhesive reservoir.

17. A kit for the treatment of an oral disease comprising the transmucosal delivery device of claim 5 and labeling or other instructions describing that (i), when needed, the backing layer may be removed after an initial amount of time of less than a recommended treatment time, or (ii) when the device has changed color to a degree, this indicates that the delivery device or the backing layer thereof may be removed.

18. The kit of claim 17, wherein the labeling or other instructions describe (i).

19. The kit of claim 17, wherein the labeling or other instructions describe (ii).

* * * * *